United States Patent [19]

Hokama et al.

[11] 4,322,414
[45] Mar. 30, 1982

[54] INDANONYL PHOSPHATES AS INSECTICIDES

[75] Inventors: Takeo Hokama, Chicago; James T. Traxler, Evanston, both of Ill.

[73] Assignee: Velsicol Chemical Corporation, Chicago, Ill.

[21] Appl. No.: 210,933

[22] Filed: Nov. 28, 1980

[51] Int. Cl.³ .................. A01N 57/12; C07F 9/177
[52] U.S. Cl. ............................. 424/214; 260/946
[58] Field of Search ....................... 260/946; 424/214

[56] References Cited

U.S. PATENT DOCUMENTS 3,839,511 10/1974 Kishino et al. ................. 260/964

FOREIGN PATENT DOCUMENTS 1175608 12/1969 United Kingdom ............... 260/946

*Primary Examiner*—Anton H. Sutto
*Attorney, Agent, or Firm*—Dietmar Olesch; Robert J. Schwarz

[57] ABSTRACT

This invention discloses new insecticidal compounds of the formula:

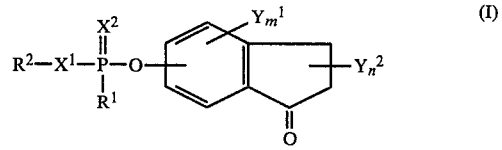

wherein each $X^1$ and $X^2$ is oxygen or sulfur; $R^1$ is selected from the group consisting of alkyl, alkenyl, alkoxy, alkythio and:

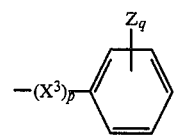

wherein $X^3$ is oxygen or sulfur, p is the integer 0 or 1, Z is selected from the group consisting of alkyl, halogen, alkoxy, alkylthio, haloalkyl and nitro, and q is an integer from 0 to 3; $R^2$ is selected from the group consisting of alkyl, alkenyl; $Y^1$ and $Y^2$ are each selected from the group consisting of alkyl, halogen, nitro, alkoxy, alkylthio and haloalkyl; and m and n are integers from 0 to 2.

9 Claims, No Drawings

INDANONYL PHOSPHATES AS INSECTICIDES

This invention relates to new compositions of matter and more specifically relates to new chemical compounds of the formula

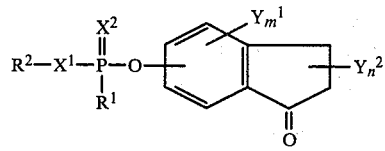  (I)

wherein each $X^1$ and $X^2$ is oxygen or sulfur; $R^1$ is selected from the group consisting of alkyl, alkenyl, alkoxy, alkylthio and

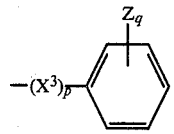

wherein $X^3$ is oxygen or sulfur, p is the integer 0 or 1, Z is selected from the group consisting of alkyl, halogen, alkoxy, alkylthio, haloalkyl and nitro, and q is an integer from 0 to 3; $R^2$ is selected from the group consisting of alkyl and alkenyl; $Y^1$ and $Y^2$ are each selected from the group consisting of alkyl, halogen, nitro, alkoxy, alkylthio, and haloalkyl; and m and n are integers from 0 to 2.

The compounds of the present invention are unexpectedly useful as insecticides.

In a preferred embodiment of the present invention $X^1$ and $X^2$ is oxygen or sulfur; $R^1$ is selected from the group consisting of lower alkyl, lower alkenyl, lower alkoxy, lower alkylthio and

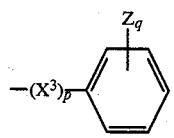

wherein $X^3$ is oxygen or sulfur, p is the integer 0 or 1, Z is selected from the group consisting of lower alkyl, halogen, lower alkoxy, lower alkylthio, lower chloroalkyl, trifluoromethyl and nitro, and q is an integer from 0 to 3; $R^2$ is selected from the group consisting of lower alkyl and lower alkenyl; $Y^1$ and $Y^2$ are each selected from the group consisting of lower alkyl, halogen, nitro, lower alkoxy, lower alkylthio and lower haloalkyl; and m and n are integers from 0 to 2.

The term lower as used herein designates a straight or branched carbon chain of up to six carbon atoms.

The compounds of the present invention can be readily prepared by reacting a phosphorus compound of the formula

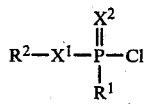  (II)

wherein $X^1$, $X^2$, $R^1$ and $R^2$ are as heretofore described with a hydroxyindanone of the formula

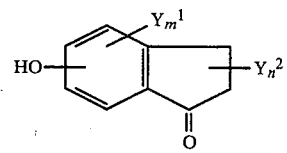  (III)

wherein $Y^1$, $Y^2$, m and n are as heretofore described. This reaction can be effected by slowly combining a solution of the phosphorus compound of formula II in an inert solvent with a solution of the hydroxyindanone of formula III in an inert solvent in the presence of an acid acceptor such as a tertiary amine at a temperature ranging from about −30° C. to about 10° C. Stirring of the reaction mixture at higher temperatures such as at room temperature for a period of 4 to 24 hours can then be utilized to insure completion of the reaction. After this time the reaction mixture can be filtered to remove acid acceptor chloride salt, washed with water, dried and stripped of solvent to yield the desired product. This product can then be used as such or can be further purified by chromatography through clay using various solvent blends as the eluant.

Both the compounds of formula II and III are known in the art. If not readily available the compounds of formula II can be prepared from the corresponding dichloride by reaction with the appropriate alcohol.

Compounds of formula III when not readily available can be prepared from a dihydrocoumarin of the formula

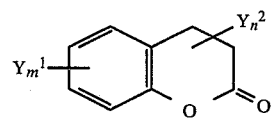  (IV)

wherein $Y^1$, $Y^2$, m and n are as heretofore described by reaction with anhydrous aluminum chloride. This reaction can be readily effected by combining the reactants followed by heating at temperatures ranging from 80° to 250° C. for periods up to several hours. This reaction can be performed in an inert atmosphere such as under nitrogen. The reaction mixture can then be washed with aqueous hydrochloric acid and the desired product can then be recovered by separation of the organic phase. This product can be used as such or can preferably be purified by distillation or chromatography.

The compounds of formula III when not readily available can be prepared by Friedel-Craft acrylation-cyclization of phenols or anesoles with 2-B-unsaturated acid chlorides or B-halopropionyl chlorides and aluminum chloride. 4-chromanones or dihydrocoumarins can also be rearranged with aluminum chloride to give 7- and 4-hydroxyindanones respectively. Alternatively, selective electrophilic substitutions can be carried out on unsubstituted hydroxyindanones to introduce desired substituent groups.

The manner in which the compounds of the present invention can be prepared is more specifically illustrated in the following examples.

EXAMPLE 1

Preparation of 4-Hydroxyindan-1-one

Dihydrocoumarin (10.5 grams; 0.07 mole) and anhydrous aluminum trichloride powder (19.0 grams; 0.14 mole) were charged into a 300 ml glass reaction flask equipped with a mechanical stirrer, thermometer and gas inlet tube. The flask was purged with nitrogen gas and the reaction mixture was slowly heated to a temperature of 200° with stirring. Heating at 200° C. and stirring were continued for a period of one hour. After this time the reaction mixture was cooled in an ice bath and aqueous hydrochloric acid (50 ml conc. HCl+50 ml $H_2O$) was added dropwise. After the addition was completed, stirring was continued at room temperature for a period of about 1 hour. After this time the reaction mixture was transferred into a separatory funnel and extracted with methylene chloride. During extraction a solid precipitate formed. The precipitate was recovered by filtration. The remaining aqueous phase was then extracted with ether and the ether extract was combined with the methylene chloride extract. The extracts were then dried over anhydrous magnesium sulfate filtered and stripped of solvents leaving a solid residue. This residue was combined with the precipitate. This material was combined with the product obtained from a repeat of the foregoing procedure and the combined products were recrystallized from methanol. The resulting product was dried under vacuum at 80° C. for about 8 hours to yield the desired product 4-hydroxyindan-1-one having a melt point of 243° C.

EXAMPLE 2

Preparation of O-Ethyl S-n-Propyl O-Indan-1-on-4-yl Thiophosphate

Acetonitrile (50 ml) and S-n-propyl dichlorothiophosphate (3.9 grams; 0.02 mole) were charged into a glass reaction vessel equipped with a magnetic stirrer, thermometer, reflux condenser, gas inlet tube and addition funnel. The reaction vessel was flushed with nitrogen gas, cooled to about −20° C. and a solution of ethanol (1.18 ml; 0.02 mole) and triethylamine (3.0 grams; 0.03 mole) in acetonitrile (20 ml) was added dropwise with stirring. After the addition was completed, stirring was continued at a temperature of about 0° C. for a period of about one and one-half hours.

The reaction mixture was allowed to warm to room temperature and a mixture of 4-hydroxyindan-1-one (2.9 grams; 0.02 mole) and triethylamine (3.0 grams; 0.03 mole) was added. The reaction mixture was then stirred at room temperature overnight. After this time, the reaction mixture was transferred to a separatory funnel and dissolved in toluene. The toluene solution was washed twice with 100 ml portions of water, was dried over anhydrous sodium sulfate, and filtered. The filtrate was then stripped of solvents under reduced pressure leaving a yellow oil as the residue. This residue was chromatographed through a 60 ml clay column using mixtures of ethyl acetate and hexane, with increasing amounts of ethyl acetate in the various fractions, as the eluant. A total of five fractions were collected and fractions 3 and 4 were combined and stripped of solvents under vacuum to yield the desired product, O-ethyl S-n-propyl O-indan-1-on-4-yl triophosphate as a yellow oil.

EXAMPLE 3

Preparation of O-Ethyl S-n-Propyl O-Indan-1-on-7-yl Thiophosphate

S-n-Propyl dichlorothiophosphate (3.2 grams; 0.0165 mole) and methylene chloride (100 ml) were charged into a glass reaction vessel equipped with a magnetic stirrer, thermometer, gas inlet tube and addition funnel. The mixture was cooled to −40° C. and a mixture of ethanol (0.8 grams; 0.017 mole), triethylamine (1.8 grams; 0.0175 mole) and methylene chloride (50 ml) was added, with stirring over a period of about 5 minutes. After the addition was completed, stirring was continued for about 30 minutes at −20° to −5° C. and for about 90 minutes at 0° to 5° C.

After this time, the reaction mixture was allowed to warm to room temperature and 7-hydroxyindan-1-one (2.2 grams, 0.015 mole) and triethylamine (1.8 grams; 0.175 mole) were added and stirred at room temperature overnight. The reaction mixture was then transferred to a separatory funnel and was washed with three 100 ml portions of water. The washed solution was passed through phase separation paper and was thereafter stripped of solvent in a rotary evaporator under water aspirator pressure leaving a reddish liquid residue. This residue was chromatographed through a clay column using ethyl acetate hexane mixtures as the eluant. Eleven 100 ml fractions were collected. Fractions 6 through 10 were combined and stripped of solvents to yield the desired product O-ethyl S-n-propyl O-indan-1-on-7-yl thiophosphate as a yellow oil.

EXAMPLE 4

Preparation of O-Ethyl S-n-Propyl O-(4-Chloroindan-1-on-7-yl) Thiophosphate

S-n-Propyl dichlorothiophosphate (3.2 grams; 0.0165 mole) and methylene chloride (100 ml) were charged into a glass reaction vessel equipped with a magnetic stirrer, thermometer, gas inlet tube and addition funnel. The reaction vessel was purged with nitrogen gas and the mixture cooled to −20° C. Ethanol (0.8 grams; 0.017 mole), triethylamine (1.8 grams; 0.0175 mole) and methylene chloride (15 ml) were added to the reaction mixture, with stirring, over a period of about 10 minutes. Stirring was continued for 1 hour at −20° to −10° C. and for 1.5 hours at 0° to 5° C.

After this time, 4-chloro-7-hydroxyindan-1-one (2.7 grams; 0.015 mole) and triethylamine (1.8 grams; 0.0175 mole) were added and the mixture was stirred at room temperature overnight. After this time the reaction mixture was washed three times with 100 ml portions of water and then dried by passing it through phase separation paper. The dried solution was then stripped of solvent in a rotary evaporator leaving an orange-red liquid residue. The residue was chromatographed through a clay column using ethyl acetate-hexane mixtures as the eluant. Fractions 5 through 7 were collected and stripped of solvents to yield the desired product O-ethyl S-n-propyl O-(4-chloroindan-1-on-7-yl) thiophosphate as a light yellow oil.

EXAMPLE 5

Preparation of 3,3-Dimethyl-7-hydroxyindan-1-one

Phenol (47 grams, 0.5 mol) and 3,3-dimethylacroyl chloride (59 grams, 0.5 mol) were charged to a glass reaction flask equipped with a magnetic stirrer, thermometer and reflux condenser. The mixture was heated at 60°–70° C. for 1 hour. The reaction mixture was cooled to room temperature and anhydrous aluminum chloride (93 grams, 0.7 mol) was added. The resulting exotherm raised the temperature to 130° C. Thereafter, the temperature of the mixture was maintained at 130°–140° C. for a period of 3 hours. After this time the mixture was allowed to cool to room temperature and aqueous hydrochloric acid (100 ml conc. HCl+100 ml $H_2O$) was added. The reaction product was then steam distilled into 6 fractions. Each fraction was extracted with methylene chloride and the resulting extracts were stripped of solvent. Fractions 3 to 6 were combined to yield the desired product, 3,3-dimethyl-7-hydroxyindan-1-one.

EXAMPLE 6

Preparation of O-Ethyl S-n-Propyl O-(3,3-Dimethylindan-1-on-7-yl) Thiophosphate S-n-Propyl dichlorothiophosphate (3.0 grams; 0.0155 mole) and dry toluene (80 mls) were charged into a glass reaction vessel equipped with a magnetic stirrer, thermometer, addition funnel and gas inlet tube. The reaction vessel was purged with nitrogen gas and the mixture was cooled to −10° C. Ethanol (0.714 grams; 0.0155 mole) and triethylamine (2.1 grams; 0.021 mole) dissolved in dry toluene (20 ml) was then added dropwise, with stirring, while maintaining the temperature below 0° C. After the addition was completed stirring was continued for a period of 2.5 hours while maintaining the temperature at 0° C.

After this time 3,3-dimethyl-7-hydroxyindan-1-one (4-grams; product of Example 5) and triethylamine (2.1 grams) dissolved in toluene (20 ml) was added dropwise with stirring. Stirring is continued for a period of about 1 hour at 0° C. after the addition was completed and at room temperature for several hours The reaction mixture was then filtered and the filtrate washed with water. The washed solution was dried and stripped of solvents leaving an amber oil as the residue. This residue was chromatographed through a 200 ml column of clay using mixtures of ethyl acetate and hexane and fractions 13, 14 and 15 were combined and stripped of solvents to yield the desired product O-ethyl S-n-propyl O-(3,4-dimethylindan-1-on-7-yl) thiophosphate as a yellow oil.

EXAMPLE 7

Preparation of O-Ethyl S-Propyl O-(4,6-Dichloroindan-1-on-7-yl) Thiophosphate S-n-Propyl dichlorothiophosphate (2.9 grams; 0.015 mole) and dry toluene (80 ml) were charged into a glass reaction vessel equipped with a magnetic stirrer, thermometer, addition funnel and gas inlet tube. The reaction vessel was purged with nitrogen gas and the reaction mixture was cooled to −10° C. Ethanol (0.69 gram; 0.015 mole) and triethylamine (2.0 grams) dissolved in dry toluene (20 ml) were then added dropwise, with stirring, while maintaining the temperature of the reaction mixture below 0° C. After the addition was completed stirring was continued for a period of 2.5 hours while maintaining the temperature at 0° C.

After this time 4,6-dichloro-7-hydroxyindan-1-one (3.25 grams; 0.015 mole) dissolved in toluene (20 ml) and triethylamine (2.0 grams) were added dropwise with stirring at 0° C. After the addition was completed stirring was continued at room temperature overnight. The reaction mixture was then filtered and the filtrate washed with water. The washed solution was dried and stripped of solvent leaving an oil as the residue. This residue was chromatographed using a 150 ml clay column and mixtures of ethyl acetate and hexane as the eluant. Ten separate fractions were collected. Fractions 4 to 7 were combined, stripped of solvent and subjected to vacuum to yield the desired product O-ethyl S-propyl O-(4,6-dichloroindan-1-on-7-yl) thiophosphate as a yellow oil.

EXAMPLE 8

Preparation of O-Ethyl S-Propyl O-(5-Chloroindan-1-on-4-yl) Thiophosphate

S-n-Propyl dichlorothiophosphate (1.6 grams; 0.0083 mole) and dry toluene (80 ml) were charged into a glass reaction vessel equipped with a magnetic stirrer, thermometer, addition funnel and gas inlet tube. The reaction vessel was purged with nitrogen gas and the reaction mixture was cooled to −10° C. Ethanol (0.382 gram; 0.0083 mole) and triethylamine (1.0 grams) dissolved in dry toluene (20 ml) were then added dropwise with stirring, while maintaining the temperature of the reaction mixture below 0° C. After the addition was completed stirring was continued for a period of 2.5 hours while maintaining the temperature at 0° C.

After this time 5-chloro-4-hydroxyindan-1-one (1.5 grams) dissolved in methylene chloride (20 ml) and triethylamine (1.0 grams) were added dropwise with stirring at 0° C. After the addition was completed stirring was continued at room temperature overnight. The reaction mixture was then filtered and the filtrate washed with water. The washed solution was dried and stripped of solvent leaving an oil as the residue. This residue was chromatographed using a 150 ml clay column and mixtures of ethyl acetate and hexane as the eluant. Ten separate fractions were collected. Fractions 4 to 7 were combined, stripped of solvent and subjected to vacuum to yield the desired product O-ethyl S-n-propyl O-(5-chloroindan-1-on-4-yl) thiophosphate as an orange oil.

EXAMPLE 9

Preparation of O-Ethyl S-Propyl O-(4-methylindan-1-on-7-yl) Thiophosphate

S-n-Propyl dichlorothiophosphate (3.6 grams; 0.0186 mole) and dry toluene (80 ml) were charged into a glass reaction vessel equipped with a magnetic stirrer, thermometer, addition funnel and gas inlet tube. The reaction vessel was purged with nitrogen gas and the reaction mixture was cooled to −10° C., Ethanol (0.085 gram; 0.0186 mole) and triethylamine (2.5 grams) dissolved in dry toluene (20 ml) was then added dropwise, with stirring, while maintaining the temperature of the reaction mixture below 0° C. After the addition was completed stirring was continued for a period of 5 hours while maintaining the temperature at 0° C.

After this time 4-methyl-7-hydroxyindan-1-one (3.0 grams; 0.0185 mole) dissolved in toluene (20 ml) and triethylamine (2.5 grams) dissolved in a small amount of methylene chloride were added dropwise with stirring at 0° C. After the addition was completed stirring was continued at room temperature overnight. The reaction mixture was then filtered and the filtrate washed with water. The washed solution was dried and stripped of solvent leaving an oil as the residue. This residue was chromatographed using a 150 ml clay column and mixtures of ethyl acetate and hexane as the eluant. Ten separate fractions were collected. Fractions 6 to 9 were combined, stripped of solvent and subjected to vacuum to yield the desired product O-ethyl S-propyl O-(4-methylindan-1-on-7-yl) thiophosphate as a yellow oil.

EXAMPLE 10

Preparation of O-Methyl S-Ethyl O-(4-Bromoindan-1-on-7-yl) Thiophosphate

O-Methyl S-ethyl chlorothiophosphate (0.015 mole) dissolved in dry toluene (80) is charged into a glass reaction vessel equipped with a stirrer, thermometer and gas inlet tube. The solution is cooled to about 0° C. and a solution of 4-bromo-7-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product O-methyl S-ethyl O-(4-bromoindan-1-on-7-yl) thiophosphate.

EXAMPLE 11

Preparation of S-Methyl O-(3-Chlorophenyl) O-(7-Methylindan-1-on-4-yl) Dithiophosphate S-Methyl O-(3-chlorophenyl) chlorodithiophosphate (0.015 mole) dissolved in dry toluene (80) is charged into a glass reaction vessel equipped with a stirrer, thermometer and gas inlet tube. The solution is cooled to about 0° C. and a solution of 7-methyl-4-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours.

After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions are then combined stripped of solvent and subjected to vacuum to yield and desired product S-methyl O-(3-chlorophenyl) O-(7-methylindan-1-on-4-yl) dithiophosphate.

EXAMPLE 12

Preparation of O-Butyl O-(3-Trifluoromethylidan-1-one-4-yl) 2-Methyl-4-bromophenylphosphate O-butyl 2-methyl-4-bromophenylphosphonyl chloride (0.015 mole) dissolved in dry toluene (80) is charged into a glass reaction vessel equipped with a stirrer, thermometer and gas inlet tube. The solution is cooled to about 0° C. and a solution of 3-trifluoromethyl-4-hydroxyindan-1-one (0.015 mole) and triethylamine (0.0175 mole) in toluene (20 ml) is slowly added in the stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product O-butyl O-(3-trifluoromethylindan-1-one-4-yl)2-methyl-4-bromophenylphosphonate.

EXAMPLE 13

Preparation of O-Allyl O-(2-Methoxyphenyl) O-(4-Trifluoromethylindan-1-on-7-yl) Phosphate O-Allyl O-(2-methoxyphenyl) chlorophosphate (0.015 mole) dissolved in dry toluene (80) is charged into a glass reaction vessel equipped with a stirrer, thermometer and gas inlet tube. The solution is cooled to about 0° C. and a solution of 4-trifluoromethyl-7-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product O-allyl O-(2-methoxyphenyl) O-(4-trifluoromethylindan-1-on-7-yl) phosphate.

EXAMPLE 14

Preparation of O-Ethyl O-t-Butyl O-(3-Chloroindan-1-on-7-yl) Phosphate

O-Ethyl O-t-butyl chlorophosphate (0.015 mole) dissolved in dry toluene (80) is charged into a glass reaction vessel equipped with a stirrer, thermometer and gas inlet tube. The solution is cooled to about 0° C. and a solution of 3-chloro-4-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product O-ethyl O-t-butyl O-(3-chloroindan-1-on-7-yl) phosphate.

EXAMPLE 15

Preparation of S-Ethyl O-(3-Methylthiophenyl) O-(7-Bromoindan-1-on-4-yl) Thiophosphate S-Ethyl O-(3-methylthiophenyl) chlorothiophosphate (0.015 mole) dissolved in dry toluene (80) is charged into a glass reaction vessel equipped with a stirrer, thermometer and gas inlet tube. The solution is cooled to about 0° C. and a solution of 7-bromo-4-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product S-ethyl O-(3-methylthiophenyl) O-(7-bromoindan-1-on-4-yl) thiophosphate.

EXAMPLE 16

Preparation of S-n-Butyl O-(4-Trifluoromethylphenyl) O-Indan-1-on-7-yl Dithiophosphate S-n-Butyl O-(4-trifluoromethylphenyl) chlorodithiophosphate (0.015 mole) dissolved in dry toluene (80) is charged into a glass reaction vessel equipped with a stirrer, thermometer and gas inlet tube. The solution is cooled to about 0° C. and a solution of 7-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product S-n-butyl O-(4-trifluoromethylphenyl) O-indan-1-on-7-yl dithiophosphate.

EXAMPLE 17

Preparation of O-Methyl S-(3-Nitrophenyl) O-Indan-1-on-7-yl Thiophosphate

O-Methyl S-(3-nitrophenyl) chlorothiophosphate (0.015 mole) dissolved in dry toluene (80) is charged into a glass reaction vessel equipped with a stirrer, thermometer and gas inlet tube. The solution is cooled to about 0° C. and a solution of 7-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product O-methyl S-(3-nitrophenyl) O-indan-1-on-7-yl thiophosphate.

EXAMPLE 18

Preparation of O-Ethyl S-Propyl O-(4-Nitroindan-1-on-7-yl) Thiophosphate

O-Ethyl S-propyl chlorothiophosphate (0.015 mole) dissolved in dry toluene (80) is charged into a glass reaction vessel equipped with a stirrer, thermometer and gas inlet tube. The solution is cooled to about 0° C. and a solution of 4-nitro-7-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product, O-ethyl S-propyl O-(4-nitroindan-1-on-7-yl) thiophosphate.

EXAMPLE 19

Preparation of O-Ethyl S-Propyl O-(7-Methoxyindan-1-on-4-yl) Thiophosphate

O-Ethyl S-propyl chlorothiophosphate (0.015 mole) dissolved in dry toluene (80) is charged into a glass reaction vessel equipped with a stirrer, thermometer and gas inlet tube. The solution is cooled to about 0° C. and a solution of 7-methoxy-4-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product, O-ethyl S-propyl O-(7-methoxyindan-1-on-4-yl) thiophosphate.

EXAMPLE 20

Preparation of O-Ethyl S-Propyl O-(7-Methylthioindan-1-on-4-yl) Thiophosphate

O-Ethyl S-propyl chlorothiophosphate (0.015 mole) dissolved in dry toluene (80) is charged into a glass reaction vessel equipped with a stirrer, thermometer and gas inlet tube. The solution is cooled to about 0° C.

and a solution of 7-methylthio-4-hydroxyindan-1-one (0.015 mole) and triethylamine (0.0175 mole) in toluene (20 ml) is slowly added with stirring. After the addition is completed the reaction mixture is allowed to warm to room temperature and stirring is continued for a period of about 8 hours. After this time the reaction mixture is filtered and the filtrate is washed with water. The washed solution is then dried and is stripped of solvent leaving a residue. This residue is chromatographed through a 200 ml clay column using ethyl acetate and hexane mixtures as the eluant. Ten separate fractions each containing increasing percentages of ethyl acetate are collected and analyzed by IR for the product. The appropriate fractions are then combined stripped of solvent and subjected to vacuum to yield the desired product O-ethyl S-propyl O-(7-methylthioindan-1-on-4-yl) thiophosphate.

Additional exemplary compounds within the scope of the present invention which can be prepared by the procedure detailed in the foregoing examples are:

O,O-dimethyl O-indan-1-on-7-yl phosphate, O,O-diethyl O-indan-1-on-7-yl phosphate, O,O-dipropyl O-indan-1-on-7-yl phosphate, O,O-dipentyl O-indan-1-on-7-yl phosphate, O,O-dihexyl O-indan-1-on-7-yl phosphate, O,S-dimethyl O-indan-1-on-7-yl thiophosphate, O,S-diethyl O-indan-1-on-7-yl thiophosphate, O,-dibutyl O-indan-1-on-7-yl thiophosphate, O,S-dihexyl O-indan-1-on-7-yl thiophosphate, S,S-dimethyl O-indan-1-on-7-yl dithiophosphate, S,S-diethyl O-indan-1-on-7-yl dithiophosphate, S,S-dipropyl O-indan-1-on-7-yl dithiophosphate, S,S-dihexyl O-indan-1-on-7-yl dithiophosphate, O-methyl O-indan-1-on-7-yl methylphosphonate, O-ethyl O-indan-1-on-7-yl ethylphosphonate, O-propyl O-indan-1-on-7-yl butylphosphonate, O-butyl O-indan-1-on-7-yl propylphosphonate, O-ethyl S-propyl O-(3-ethylindan-1-on-4-yl) thiophosphate, O-ethyl O-propyl O-(3-propylindan-1-on-4-yl) thiophosphate, O-ethyl S-propyl O-(3-butylindan-1-on-4-yl) thiophosphate, O-ethyl S-propyl O-(3-hexylindan-1-on-4-yl) thiophosphate, O-ethyl S-propyl O-(3-fluoroindan-1-on-4-yl) thiophosphate, O-ethyl S-propyl O-(3-chloromethylindan-1-on-4-yl) thiophosphate, O-ethyl S-propyl O-(3-B-chloroethylindan-1-on-4-yl) thiophosphate O-ethyl S-propyl O-(7-ethylindan-1-on-4-yl) thiophospate, O-ethyl S-propyl O-(7-propylindan-1-on-4-yl) thiophosphate, O-ethyl S-propyl O-(7-chloromethylindan-1-on-4-yl) thiophosphate, O-ethyl S-propyl O-(7-bromoindan-1-on-4-yl) thiophosphate, O-ethyl S-propyl O-(7-fluoroindan-1-on-4-yl) thiophosphate, O-but-3-enyl S-propyl O-(4-chloroindan-1-on-7-yl) thiophosphate, O-pent-4-enyl S-propyl O-(3,4-dichloroindan-1-on-7-yl) thiophosphate, O-hex-4-enyl S-propyl O-(3,4,5-trichloroindan-1-on-7-yl), thiophosphate, O-methyl O-(2-ethylpropyl) O-indan-1-on-4-yl phosphate, O-methyl O-(3-propylphenyl) O-indan-1-on-4-yl phosphate, O-methyl O-(4-butylphenyl) O-indan-1-on-4-yl phosphate, O-methyl O-(4-hexylphenyl) O-indan-1-on-4-yl phosphate, O-methyl O-(4-fluorophenyl) O-indan-1-on-4-yl phosphate, O-methyl O-(3-iodophenyl) O-indan-1-on-4-yl phosphate, O-methyl O-(3-ethoxyphenyl) O-indan-1-on-4-yl phosphate, O-methyl O-(4-propoxyphenyl) O-indan-1-on-4-yl phosphate, O-methyl O-(4-butoxyphenyl) O-indan-1-on-4-yl thiophosphate, O-methyl O-(3-hexyloxyphenyl) O-indan-1-on-4-yl thiophosphate, S-(3-ethylthiophenyl) O-indan-1-on-4-yl thiophosphate, S-(4-propylthiophenyl) O-indan-1-on-4-yl thiophosphate, S-(4-hexylthiophenyl) O-indan-1-on-4-yl dithiophosphate, S-(3-bromomethylphenyl) O-indan-1-on-4-yl dithiophosphate, S-(4-B-chloroethylphenyl) O-indan-1-on-4-yl dithiophosphate, S-ethyl S-(4-B-chloropropyl) O-indan-1-on-4-yl trithiophosphate, O-ethyl O-indan-1-on-7-yl 2-methylphenylphosphonate, O-ethyl O-indan-1-on-7-yl 2-methyl-4-chlorophosphonate, O-ethyl O-indan-1-on-7-yl 3,4-dichlorophenylphosphonate, O-ethyl O-indan-1-on-7-yl, 3,4,5-trichlorophenylphosphonate, S-ethyl O-indan-1-on-7-yl propylthiophosphonate, S-propyl O-indan-1-on-7-yl ethylthiophosphonate and the like.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophylite and the like. Granular formulations can be prepared by impregnating the compound, usually dissolved in a suitable solvent, onto and into granulated carriers such as the attapulgites or the vermiculites, usually of a particle size ranging from about 0.3 to 1.5 mm. Wettable powders, which can be dispersed in water and/or oil to any desired concentration of the active compound, can be prepared by incorporating wetting agents into concentrated dust compositions.

In some cases, the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates which comprise an active compound according to this invention and as the inert carrier a solvent and an emulsifier. Such emulsifiable concentrates can be extended with water for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 21

PREPARATION OF A DUST

Product of Example 2—10
Powdered talc—90

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal composition to control insects, can include halogenated compounds such as DDT, methoxychlor, TDE, lindane, chlordane, isobenzan, aldrin, dieldrin, heptachlor, endrin mirex, endosulfon, dicofol and the like; organic phosphorus compounds such as TEPP, schradan, ethion, parathion, PEN, demeton carbophenothion phorate, zinophos, diazinon, malathion, mevinphos, dimethoate, DBD, ronnel, oxydemeton-methyl, dicapthon, chlorothion, phosphamidon, naled, fenthion, trichlorofon, DDVP, and the like; organic nitrogen compound such as dinitro-o-cresol, dinitrocyclohexylphenol, DNB, DNP, binapacril, azobenzene and the like; organic sulfur compounds such as phenothiazine, phenoxathin, lauryl thiocyanate, bis(2-thiocyanoethyl)ether, isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of the fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systematically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beatle and the southern armyworm; the piercing-sucking insects, such as the peak aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the woolly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding while a pound or more of active compound per acre may be required for the control of a heavy infestation of insects under conditions favorable to their development.

The insecticidal activity of the compounds of the present invention was demonstrated by experiments carried out for the control of a variety of insects. In these experiments, the compounds to be tested are first put into a formulation suitable for application at various concentrations and application rates to plants and insects. The desired quantity of the test compound (the quantity being determined by the application concentration or application rate to be used in later testing) is dissolved or dispersed in a solvent consisting of acetone containing 3.19 grams/liter of Triton X-155 per liter.

Test plants used in these experiments are prepared by planting the appropriate seeds in sterilized soil contained in plastic pots having an upper soil surface area of approximately 12.25 square inches (aswuare pot having a 3.5 inch side). After the seed has been planted, a layer of approximately 0.25 inches of sand is spread on the top surface of the soil. The test compound is applied after the plant has reached a specified size.

For the foliar applications, the test compound, dissolved or dispersed in the water/acetone solvent described above, is sprayed as a mist onto the foliage of the test plants. The concentration of the test compound and the total quantity of solution applied is adjusted to give the application concentrations or rates desired. The plants are then allowed to air dry. Mites and aphids are exposed to treated leaves which have been left on the plant. Other insect species are exposed to treated leaves which have been removed from the plant and placed in petri dishes containing a piece of moist filter paper.

For soil drench applications the test compound is first dissolved or dispersed in water/acetone as described above, then the amount of solution required to give a desired application rate is applied, using a pipette, evenly over the top of the soil in the pot. Twenty four hours after the treatment, mites and aphids are exposed to leaves which have been removed from the plants 24 hours after treatment and placed in petri dishes containing a piece of moist filter paper.

In direct contact applications, the test compound is, again, first formulated into a water/acetone solution, as described above, in the concentrations to be tested. Then the insect to be tested is dipped into, sprayed with or immersed in the liquid, dried, and observed for effect.

In the tables below setting forth the experimental data, PPM represents foliar application rates expressed as parts-per-million, #/A represents soil drench application rates expressed as pounds per acre.

CABBAGE LOOPER

Bush lima bean plants (Burpee Variety 222), two-leaf stage, are exposed, at various application rates, to the test compound applied as a foliar spray. Leaves are removed from the plants after approximately 30 minutes of air-drying of the foliar spray application, and placed in petri dishes containing a piece of moist filter paper. Ten cabbage loopers, second instar larval stage, are placed in each petri dish and the dish covered. Observations of insect mortality are made after 48 hours of exposure. Results of these tests are detailed in Table 1 below.

TABLE 1

| Test Compound | Percent Control Application Rate: PPM | | | | | | |
|---|---|---|---|---|---|---|---|
| | 256 | 128 | 64 | 32 | 16 | 8 | 4 |
| Product of Ex. 2 | 100 | 90 | 90 | 60 | — | — | — |
| Product of Ex. 3 | 100 | 80 | 70 | 90 | — | — | — |
| Product of Ex. 4 | 100 | 100 | 80 | 30 | — | — | — |
| Product of Ex. 6 | 100 | 70 | 60 | 60 | — | — | — |
| Product of Ex. 7 | 100 | 100 | 100 | 70 | 80 | 50 | 60 |
| Product of Ex. 8 | 100 | 100 | 100 | 80 | 90 | 60 | 90 |
| Product of Ex. 9 | 100 | 100 | 60 | 80 | 20 | — | — |

SOUTHERN ARMYWORM

Bush lima bean plants (Burpee Variety 222), two-leaf stage, are exposed, at various application rates, to the test compound as a foliar spray. Leaves are removed from the plants after approximately 30 minutes of air-drying of the foliar spray application and placed in petri dishes containing a piece of moist filter paper. Ten southern armyworms, second instar larval stage, are placed in each petri dish and the dish covered. Observations of insect mortality are made after 48 hours of exposure. Results of these tests are detailed in Table 2 below:

TABLE 2

| Test Compound | Percent Control Application Rate: PPM | | | | | | |
|---|---|---|---|---|---|---|---|
| | 256 | 128 | 64 | 32 | 16 | 8 | 4 |
| Product of Ex. 2 | 100 | 70 | 10 | 0 | — | — | — |
| Product of Ex. 3 | 100 | 100 | 70 | 30 | — | — | — |
| Product of Ex. 4 | 100 | 100 | 40 | 20 | — | — | — |
| Product of Ex. 6 | 100 | 100 | 20 | 20 | — | — | — |
| Product of Ex. 7 | 100 | 100 | 100 | 70 | 0 | 0 | 10 |
| Product of Ex. 8 | 100 | 100 | 100 | 90 | 0 | 0 | 0 |
| Product of Ex. 9 | 100 | 100 | 30 | 10 | 10 | — | — |

SOYBEAN LOOPER

Bush lima bean plants (Burpee Variety 222), two-leaf stage, are exposed, at various application rates, to the test compound applied as a foliar spray. Leaves are removed from the plants after approximately 30 minutes of air-drying of the foliar spray application and placed in petri dish containing a piece of moist filter paper. Ten second instar larval soybean loopers are placed in each petri dish and the dish covered. Observations of insect mortality are made after 48 hours of exposure. Results of these test results are detailed in Table 3 below:

TABLE 3

| Test Compound | Percent Control Application Rate: PPM | | | | | | |
|---|---|---|---|---|---|---|---|
| | 256 | 128 | 64 | 32 | 16 | 8 | 4 |
| Product of Ex. 2 | 100 | 40 | 20 | 0 | — | — | — |
| Product of Ex. 3 | 100 | 30 | 20 | 20 | — | — | — |
| Product of Ex. 4 | 80 | 60 | 10 | 10 | — | — | — |
| Product of Ex. 6 | 100 | 100 | 20 | 20 | — | — | — |
| Product of Ex. 7 | 100 | 100 | 30 | 20 | 70 | 40 | 60 |
| Product of Ex. 8 | 100 | 90 | 90 | 40 | 70 | 60 | 30 |
| Product of Ex. 9 | 90 | 70 | 90 | 60 | 10 | — | — |

TOBACCO BUDWORM

Bush lima bean plants (Burpee Variety 222), two-leaf stage, are exposed, at various application rates, to the test compound applied as a foliar spray. Leaves are removed from the plants after approximately 30 minutes of air-drying of the foliar spray application and placed in petri dishes containing a piece of moist filter paper. Ten tobacco budworms, second instar larval stage, are placed in each petri dish and the dish covered. Observations of insect mortality are made after 48 hours of exposure. Results of these tests are detailed in Table 4 below.

TABLE 4

| Test Compound | Percent Control Application Rate: PPM | | | | | | |
|---|---|---|---|---|---|---|---|
| | 256 | 128 | 64 | 32 | 16 | 8 | 4 |
| Product of Ex. 2 | 20 | 20 | 10 | 0 | — | — | — |
| Product of Ex. 3 | 70 | 40 | 40 | 40 | — | — | — |
| Product of Ex. 4 | 100 | 90 | 90 | 30 | — | — | — |
| Product of Ex. 6 | 70 | 20 | 10 | 0 | — | — | — |
| Product of Ex. 7 | 90 | 80 | 0 | 0 | 0 | 0 | 0 |
| Product of Ex. 8 | 60 | 10 | 20 | 0 | 0 | 0 | 0 |
| Product of Ex. 9 | 30 | 80 | 20 | 20 | 0 | — | — |

MEXICAN BEAN BEETLE

Bush lima bean plants (Burpee Variety 222), two-leaf stage, are exposed, at various application rates, to the test compound applied as foliar spray. Leaves are removed from the plants after approximately 30 minutes of air-drying of the foliar spray application and placed in petri dishes containing a piece of moist filter paper. Ten mexican bean beetles, second instar larval stage, are placed in each petri dish and the dish covered. Observations of insect mortality are made after 48 hours of exposure. Results of these tests are detailed in Table 5 below.

TABLE 5

| Test Compound | Percent Control Application Rate: PPM | | | |
|---|---|---|---|---|
| | 256 | 128 | 64 | 32 |
| Product of Ex. 2 | 40 | — | — | — |
| Product of Ex. 3 | 100 | — | — | — |
| Product of Ex. 4 | 100 | — | — | — |
| Product of Ex. 6 | — | 70 | 60 | 0 |
| Product of Ex. 7 | — | 100 | 90 | 60 |
| Product of Ex. 8 | — | 100 | 40 | 40 |
| Product of Ex. 9 | 80 | — | — | — |

BOLL WEEVIL

Cotton plants (Deltapine 16), two-leaf stage, are exposed, at various application rates, to the test compound applied as a foliar spray. Leaves are removed from the plants after approximately 30 minutes of air-drying of the foliar spray application and placed in petri dishes containing a piece of moist filter paper. Ten adult boll weevils are placed in each petri dish and the dish is then covered. Observations of insect mortality are made after 48 hours of exposure. Results of these tests are detailed in Table 6 below.

TABLE 6

| Test Compound | Percent Control Application Rate: PPM | | | |
|---|---|---|---|---|
| | 256 | 128 | 64 | 32 |
| Product of Ex. 2 | 0 | — | — | — |
| Product of Ex. 3 | 50 | — | — | — |
| Product of Ex. 4 | 10 | — | — | — |
| Product of Ex. 6 | — | 0 | 0 | 0 |
| Product of Ex. 7 | — | 0 | 0 | 0 |
| Product of Ex. 8 | — | 0 | 0 | 0 |
| Product of Ex. 9 | 0 | — | — | — |

PEA APHID

Pea plants (Burpee Wando) in the 10–14 day stage are treated with the test compound, at various application rates, foliar spray. The plants are air dried for about 30 minutes after the foliar spray is applied, then 25–50 pea aphids, adults and nymphs, are put on each treated plant and on an untreated control plant with a small paint brush. After 48 hours of exposure of the insects to the treated plants, insect mortality is determined by comparison of the number of insects on the treated plants to the number of the untreated control plant. Results of this testing are set forth in Table 7 below.

TABLE 7

| Test Compound | Percent Control Application Rate: PPM | | | |
|---|---|---|---|---|
| | 256 | 128 | 64 | 32 |
| Product of Ex. 2 | 0 | — | — | — |
| Product of Ex. 3 | 80 | — | — | — |
| Product of Ex. 4 | 90 | — | — | — |
| Product of Ex. 6 | — | 0 | 0 | 0 |
| Product of Ex. 7 | — | 0 | 0 | 0 |
| Product of Ex. 8 | — | 0 | 0 | 0 |
| Product of Ex. 9 | 100 | — | — | — |

TWO SPOTTED MITE

Bush lima bean plants (Burpee Variety 222) in the two-leaf stage are treated with the test compound, at various application rates, by the foliar spray method. The plants are air dried for about 30 minutes after the foliar spray is applied, then 50–100 two spotted mites, adults and nymphs, are put on each treated plant and on an untreated control plant by placing an untreated infested bean leaf containing 50–100 mites using the technique described above. An untreated control plant is similarly infested. After 48 hours of exposure of the insects to the treated plants, insect mortality is determined by comparison of the number of insects on the treated plants to the number on the untreated control plants. Results of this testing are set forth in Table 8 below.

TABLE 8

| Test Compound | Percent Control Application Rate: PPM | | | |
|---|---|---|---|---|
| | 256 | 128 | 64 | 32 |
| Product of Ex. 2 | 100 | — | — | — |
| Product of Ex. 3 | 100 | — | — | — |
| Product of Ex. 4 | 100 | — | — | — |
| Product of Ex. 6 | — | 80 | 30 | 10 |
| Product of Ex. 7 | — | 90 | 80 | 80 |
| Product of Ex. 8 | — | 100 | 100 | 30 |
| Product of Ex. 9 | 90 | — | — | — |

HOUSEFLY

Ten adult Houseflies are placed in a small (2"–3") wire screen cage fitted with a plastic cap. The cage is sprayed with the test compound at the desired concentration in the form of a solution prepared as described hereinabove. After spraying, the treated cages are stored until dry. Sixty minutes after spraying, readings are made of knock down. The cages are then placed on paper toweling moistened with 5–10% sucrose solution and stored on this toweling for 23 hours at which time the 24 hours-after-treatment mortality reading is taken. The results of this test are given in Table 9 below.

TABLE 9

| Test Compound | | Percent Control Application Rate: PPM | | | |
|---|---|---|---|---|---|
| | | 256 | 128 | 64 | 32 |
| Product of Ex. 2 | k | 0 | — | — | — |
| | m | 0 | — | — | — |
| Product of Ex. 3 | k | 30 | — | — | — |
| | m | 0 | — | — | — |
| Product of Ex. 4 | k | 50 | — | — | — |
| | m | 10 | — | — | — |
| Product of Ex. 6 | k | — | 70 | 10 | 20 |
| | m | — | 60 | 50 | 50 |
| Product of Ex. 7 | k | — | 0 | 0 | 0 |
| | m | — | 50 | 40 | 20 |
| Product of Ex. 8 | k | — | 80 | 10 | 0 |
| | m | — | 80 | 40 | 30 |

NOTE:
k = 60-minute knockdown
m = 24-hour mortality

GERMAN COCKROACH

Solutions of test compounds are formulated as described hereinbefore and the solution which gives a desired application concentration is placed in a flask. Ten german cockroach adults are placed in a teaspoon test strainer and are dipped into the test solution. The excess solution is shaken off, the tea strainer opened and the insects placed in a clear plastic container containing a small moist piece of dental wick. The container then is capped with a cover pierced with air holes. Insect mortality if observed after 60 minutes, 24 hours and 48 hours following the exposure. Results of this testing are indicated in Table 10 below.

TABLE 10

| Test Compound | | Percent Control Application Rate: PPM | | | |
|---|---|---|---|---|---|
| | | 256 | 128 | 64 | 32 |
| Product of Ex. 2 | (60) | 0 | | | |
| | (24) | 10 | | | |
| | (48) | 20 | | | |
| Product of Ex. 3 | (60) | 0 | | | |
| | (24) | 100 | | | |
| | (48) | 100 | | | |
| Product of Ex. 4 | (60) | 10 | | | |
| | (24) | 100 | | | |
| | (48) | 100 | | | |
| Product of Ex. 6 | (60) | | 0 | 10 | 0 |
| | (24) | | 40 | 10 | 0 |
| | (48) | | 50 | 10 | 0 |
| Product of Ex. 7 | (60) | | 80 | 0 | 0 |
| | (24) | | 100 | 90 | 40 |
| | (48) | | 100 | 90 | 50 |
| Product of Ex. 8 | (60) | | 0 | 0 | 0 |
| | (24) | | 40 | 10 | 0 |
| | (48) | | 40 | 20 | 0 |
| Product of Ex. 9 | (60) | 0 | | | |
| | (24) | 90 | | | |
| | (48) | 90 | | | |

NOTE:
(60) = 60-minute mortality
(24) = 24-hour mortality
(48) = 48-hour mortality

SOUTHERN CORN ROOTWORM

A newly germinated corn seed is placed in a one ounce plastic cup fitted with a snap-on plastic lid and covered with approximately 5 grams of sterilized soil. The test compound is formulated into solutions as described hereinbefore and applied to the soil as a soil drench at the desired application rates. After application, the lids are snapped on the cups and the cups are allowed to stand for about 15 minutes to permit the solution to spread evenly through the soil. The lids are then removed, five second instar rootworm larvae are placed on the treated soil and the cups recapped. The cup is examined for insects mortality after 72 hours of exposure. Larvae which cannot crawl or right themselves are considered dead. Results of this testing are given in Table 11 below.

TABLE 11

| Test Compound | Percent Control Application Rate: #/A | | | | | | |
|---|---|---|---|---|---|---|---|
| | 16 | 8 | 4 | 2 | 1 | 0.5 | 0.25 |
| Product of Ex. 2 | | 20 | | | | | |
| Product of Ex. 3 | | 10 | | | | | |
| Product of Ex. 4 | | 50 | | | | | |
| Product of Ex. 6 | 100 | 100 | 90 | 70 | 70 | 70 | 50 |
| Product of Ex. 7 | 100 | 80 | 85* | 50 | 50 | 50 | 60 |
| Product of Ex. 8 | 80 | 30 | 50 | | | | |
| Product of Ex. 9 | 60 | | | | | | |

NOTE:
*Average of two tests

We claim:

1. A compound of the formula:

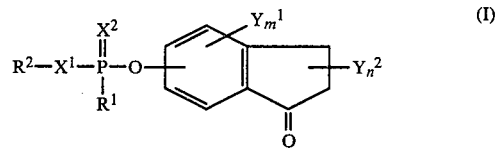

wherein each $X^1$ and $X^2$ is oxygen or sulfur; $R^1$ is selected from the group consisting of alkyl, alkenyl, alkoxy, alkylthio and:

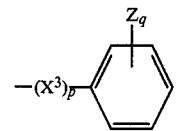

wherein $X^3$ is oxygen or sulfur, p is the integer 0 or 1, Z is selected from the group consisting of alkyl, halogen, alkoxy, alkylthio, haloalkyl and nitro, and q is an integer from 0 to 3; $R^2$ is selected from the group consisting of alkyl and alkenyl; $Y^1$ and $Y^2$ are each selected from the group consisting of alkyl, halogen, nitro, alkoxy, alkylthio and haloalkyl; and m and n are integers from 0 to 2.

2. The compound of claim 1, O-ethyl S-n-propyl O-indan-1-on-4-yl thiophosphate.

3. The compound of claim 1, O-ethyl S-n-propyl O-indan-1-on-7-yl thiophosphate.

4. The compound of claim 1, O-ethyl S-n-propyl O-(4-chloroindan-1-on-7-yl) thiophosphate.

5. The compound of claim 1, O-ethyl S-n-propyl O-(3,3-dimethylindan-1-on-7-yl) thiophosphate.

6. The compound of claim 1, O-ethyl S-propyl O-(4,6-dichloroindan-1-on-7-yl) thiophosphate.

7. The compound of claim 1, O-ethyl S-propyl O-(5-chloroindan-1-on-4-yl) thiophosphate.

8. An insecticidal composition comprising an inert carrier and, as an essential active ingredient, in a quantity toxic to insects, a compound of claim 1.

9. A method of controlling insects which comprises contacting said insects with an insecticidal composition comprising an inert carrier and, as an essential active ingredient, in a quantity toxic to insects, a compound of claim 1.

* * * * *